United States Patent
Thakur

(10) Patent No.: US 7,641,977 B2
(45) Date of Patent: Jan. 5, 2010

(54) APPLICATIONS OF NONCONJUGATED CONDUCTIVE POLYMERS

(76) Inventor: Mrinal Thakur, 971 Law Dr., Auburn, AL (US) 36830-2883

( * ) Notice: Subject to any disclaimer, the term of this patent is extended or adjusted under 35 U.S.C. 154(b) by 243 days.

(21) Appl. No.: 11/046,173

(22) Filed: Jan. 28, 2005

(65) Prior Publication Data

US 2005/0163918 A1 Jul. 28, 2005

Related U.S. Application Data

(60) Provisional application No. 60/539,803, filed on Jan. 28, 2004.

(51) Int. Cl.
*B32B 17/06* (2006.01)
(52) U.S. Cl. .................. 428/432; 428/433; 428/440; 428/441; 428/461; 428/462
(58) Field of Classification Search ............... 428/461, 428/462, 432, 433, 440, 441
See application file for complete search history.

(56) References Cited

U.S. PATENT DOCUMENTS

| 4,765,928 | A | 8/1988 | Thakur ................. 252/500 |
| 7,170,086 | B2 * | 1/2007 | Suh et al. .............. 257/40 |
| 7,455,916 | B2 * | 11/2008 | Hirose et al. ........... 428/690 |
| 2005/0048314 | A1 * | 3/2005 | Antoniadis et al. ....... 428/690 |

OTHER PUBLICATIONS

"Optical and magnetic properties of a nonconjugated conducting polymer", M. Thakur and B.S. Elman, *J. Chem. Phys.* vol. 90, No. 3, Feb. 1, 1989, p. 2042.

"Poly(*p*-phenylenevinylene) light-emitting diodes: Enhanced electroluminescent efficiency through charge carrier confinement", A.R. Brown, et al., *Appl. Phys. Lett.*, vol. 61, No. 23, Dec. 7, 1992, p. 2794-95.
"Electroabsorption of polyacetylene", S.D. Phillips, et al., *The American Physical Society*, vol. 40, No. 14, Nov. 15, 1989, pp. 9751-9759.
"A Class of Conducting Polymers Having Nonconjugated Backbones", M. Thakur, Macromolecules 1988, 21, pp. 661-664.

* cited by examiner

*Primary Examiner*—D. S Nakarani
(74) *Attorney, Agent, or Firm*—Thomas, Kayden, Horstemeyer & Risley LLP

(57) ABSTRACT

Nonconjugated conductive polymers, which are all polymers that have a ratio of double bonds to total bonds of less than ½ are doped or used to produce compositions with unexpected characteristics in this invention. A light emitting structure can be produced by coating a quartz or glass substrate with a high work function metal which has a nonconjugated conductive polymer film on the metal and a low work function metal deposited on the nonconjugated polymer. The electrical conductivity of nonconjugated polymers can be greatly increased by doping the polymer with a dopant. The mechanical and elastomeric properties of a nonconjugated polymer can be changed by doping the polymer. The electro-optic effect and the refractive index of a nonconjugated conductive polymer can be greatly changed by doping the polymer. Among the nonconjugated polymers are styrene-butadiene-rubber (SBR), poly(β-pinene) and cis-1-4 polyisoprene. The enhancement of the nonlinear optical effect is due to the special charge-transfer complex structure and formation of nano-optical domains. Among the doping materials are electron acceptors such as iodine and antimony pentachloride. A heated mixture of iodine and sulfur produces a faster rate of vulcanization of rubber than using sulfur alone. A method of controlling insect breeding is provided which involves exposing the insects to tires that have been vulcanized using iodine.

12 Claims, 2 Drawing Sheets

Electric field-induced light emission in a nonconjugated conductive polymer. (Higher field)

Fig.1 Electric field-induced light emission in a nonconjugated conductive polymer (Lower field)
Fig.2 Electric field-induced light emission in a nonconjugated conductive polymer. (Higher field)

US 7,641,977 B2

APPLICATIONS OF NONCONJUGATED CONDUCTIVE POLYMERS

CROSS-REFERENCE TO RELATED APPLICATION

This application claims priority to copending U.S. provisional application entitled, "NOVEL APPLICATIONS OF NONCONJUGATED CONDUCTIVE POLYMERS," having Ser. No. 60/539,803, filed Jan. 28, 2004, which is entirely incorporated herein by reference.

BACKGROUND OF THE INVENTION

Field of the Invention

This invention relates to novel applications of nonconjugated conductive polymers. Nonconjugated conductive polymers have at least one double bond which is repeated in a ratio of double bond to total bonds that is a lower fraction than ½. It has been found that these polymers have novel light emission, nonlinear optical and mechanical properties.

SUMMARY OF THE INVENTION

Plastics/polymers have a wide range of applications. In this disclosure, three types of novel applications of nonconjugated conductive polymers are discussed. These classes of applications include: (i) light emitting devices, (ii) nonlinear optical devices and (iii) specific structures requiring enhanced mechanical properties. Conjugated polymers have a repeat with one double bond followed by a single bond, which is followed by another double bond and a single bond. Thus, there is a ratio of double bonds to total bonds, ½. Nonconjugated conductive polymers include polymers with at least one double bond in the repeat. Nonconjugated polymers include all of those polymers that have a ratio of double bond to total bonds, that is a lower fraction than ½. It includes polymers where there is only one double bond in each repeat. It will be recognized that there can be two or more double bonds in the repeat if the ratio of double bonds and total bonds is lower than "½." Upon doping, a charge-transfer takes place between the isolated double bond of the polymer and the dopant. For example, in the case of iodine doping, an electron is transferred from the double bond to iodine, thus, creating a radical cation consisting of a hole or positive charge and a radical at the double bond site. This hole then participates in the electrical conductivity through intersite hopping. The conductivity increases by about 100 billion times upon doping. The three classes of novel applications that were unexpectedly observed in nonconjugated conductive polymers are discussed in this invention.

It has been found that by doping these nonconjugated polymers with iodine and curing or vulcanizing, that unusual and novel materials and properties are obtained as explained infra.

BRIEF DESCRIPTION OF THE DRAWINGS

FIG. 1 is an electric field-induced light emission in a nonconjugated conductive polymer (lower electric field).

FIG. 2 is an electric field-induced light emission in a nonconjugated conductive polymer (higher electric field).

DETAILED DESCRIPTION OF THE PREFERRED EMBODIMENTS

Light Emission

Figure 3:
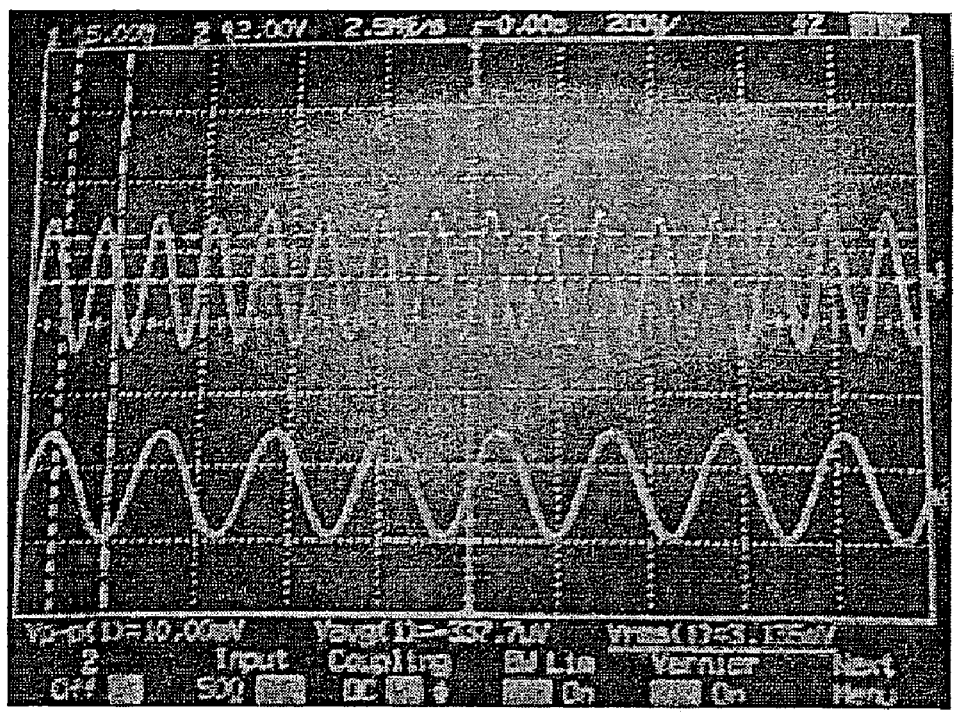
FIG. 3 show the oscilloscope trace of modulation due to quadratic electro-optic effect in iodine-doped polyisoprene. The upper waveform represents the modulation and the lower waveform represents the applied voltage.

Significant attention has been paid to light emitting devices such as light emitting diodes based on conjugated conductive polymers in view of a wide range of commercial applications. These applications include display devices and lasers among others. The basic mechanism of such devices includes electron and hole injection into a polymer film from opposite sides leading to electron-hole recombination and consequent emission of light or photons. The wavelength of the emitted light usually corresponds to the photoluminescence maximum of the polymer. The injection of electrons and holes is achieved using junctions with metals of appropriate work functions and applying an external voltage. For hole injection, a metal with a higher work function than the polymer is needed, while for electron injection a metal with a lower work function is used. Therefore, in such a device an assembly or a junction involving "metal with high work function/polymer/metal with a lower work function" is fabricated.

While specific conjugated polymers have been shown to form light emitting devices, the distinct feature of the present invention is that it involves nonconjugated conductive polymers. Conjugated polymers have alternating double and single bonds in their backbones leading to delocalization of electrons while nonconjugated conductive polymers have isolated double bonds or localized electronic states. Since nonconjugated polymers do not have delocalized electrons they do not absorb significantly in the visible domain—therefore these are colorless materials. In contrast, conjugated polymers having extensive delocalization are colored—absorbs fairly strongly in the visible domain.

It has been the general perception in the conductive polymers research community that nonconjugated polymers having no delocalized electrons can not be formed as light emitting devices. The possibility of light emitting devices based on nonconjugated polymers has been generally dismissed and consequently there is no previous work or report on light emission using nonconjugated polymers. Therefore, it is totally unexpected and surprising to be able to obtain significant light emission using nonconjugated polymers.

The general and the most basic embodiment of this invention in light emission involves a junction device or assembly consisting of a metal of high work function/nonconjugated conductive polymer/low work function metal. Specifically, a polymer thin film is formed on a quartz substrate coated with indium tin oxide (ITO) layer which acts as a high work function metal. A thin film of a low work function metal such as aluminum, calcium or magnesium is subsequently deposited on the nonconjugated polymer. A voltage is applied on the conductors (ITO and for example aluminum) of the junction device (e.g. ITO/nonconjugated polymer/Al). Light is emitted as the voltage is applied. The emitted power is proportional to the voltage or the current. A broad variation of this basic device structure for higher efficiency can be accomplished using additional intermediate layers such as electron transporting and hole transporting layers.

In the present invention, the major nonconjugated polymer structures that have been investigated include styrene-butadiene-rubber copolymer and poly(β-pinene). These polymers have photoluminescence peaks near 400 nm. The peak emission in the light emitting device formed using this polymer occurs in the violet-blue region (at about 400 nm). A wide variation of the molecular structure of the nonconjugated polymer should be possible to successfully produce novel and highly efficient light emitting devices at various wavelengths. The light emission capability is certainly not limited to only the two nonconjugated polymers described above.

If a light emitting diode is placed between two mirrors it may lead to lasing under favorable alignment and other conditions. Lasing occurs when population inversion is achieved above certain pump or current threshold and the overall gain exceeds the overall loss. The light emitting devices disclosed here can be extended to electrically-pumped lasers with appropriate modification of structures, in particular, through including two mirrors on the opposite sides forming a cavity. Therefore, the light emission capability of devices made with nonconjugated polymers is in no way limited to the results described in this invention.

Nonlinear Optical Applications

Large nonlinear optical susceptibilities, in particular, third order optical susceptibilities are usually observed in conjugated polymers. The large susceptibilities are due to delocalization of electrons along the conjugated chain. In contrast, nonconjugated polymers with isolated double bonds do not have delocalized electrons and are not expected to display significant nonlinear optical effects. In this disclosure, exceptionally large nonlinear optical susceptibilities of specific nonconjugated conductive polymers are discussed. This observation is unexpected based on existing results and understanding based on conjugated conductive polymers. As it will be shown, doped nonconjugated conductive polymers have significantly larger nonlinear optical susceptibilities than most other nonlinear optical materials including doped conjugated conductive polymers.

The nonlinear optical effects that will be disclosed include: (i) Quadratic electro-optic effect and (ii) all-optical effect. In (i) the refractive index of the nonlinear optical material changes quadratically with an applied electric field. In (ii) the refractive index changes linearly with the intensity of an optical beam. The changes in the refractive index is measured using standard optical techniques.

The nonconjugated conductive polymers which have been investigated in detail include: cis-1,4 polyisoprene and poly (β-pinene). The observation as disclosed here can be extended to all other nonconjugated conductive polymers since all nonconjugated conductive polymers are soluble and processable.

A wide range of applications are expected based on the electro-optic and all-optical effects. These include applications in research equipments (Kerr Cells), in signal processing and telecommunication, beam steering, spatial light modulators, optical computing and many others. The mechanisms of the applications involve modulating the phase or intensity of an optical beam using an external electric field or the intensity of another optical beam.

The measured large quadratic electro-optic effect has been attributed to the hole (positive charge) loosely bound to the acceptor molecule in the doped film. The loosely bound positive charge can be modeled as a spring-mass system with a quadratic term in the potential energy. As it is well known, the quadratic and cubic terms in the harmonic oscillator potential energy lead to the first order and second order optical susceptibilities respectively. The quartic term leads to the third order optical susceptibility or the quadratic electro-optic effect. The contribution of the quartic term for a loose spring can be significant leading to exceptionally large third order optical effects in this system. The material being isotropic, the cubic term is not present and therefore it does not display second order optical or linear electro-optic effect. The third order optical or the quartic electro-optic effect is large because of the higher magnitude of the quartic term and also due to the confinement of the charge within a nanometer dimension. Thus doped nonconjugated conductive polymers represent a new class of nano-optical materials. As it is well known, nanomaterials, nanodevices and nanotechnology are presently highly active areas of research. Doped polyisoprene has special charge-transfer complex structures and confinement within a nanometer domain (somewhat similar to nanometallics). This leads to the exceptionally large quadratic electro-optic effect or third order optical property of this nano-optical polymer as shown below:

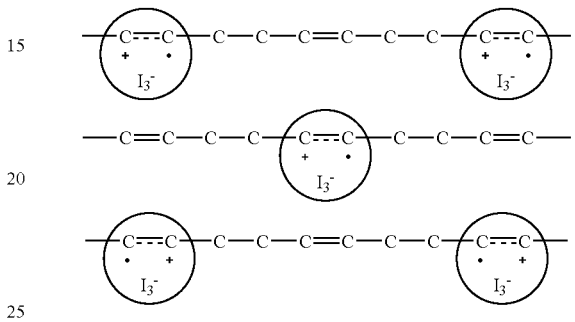

These nano-polymers can be doped with an electron acceptor, such as iodine or antimony pentachloride.

Enhanced Mechanical and Elastomeric Properties

Polymers have a wide range of mechanical and structural applications. Depending on applications, the strength, flexibility, elastic deformability and easy processing are used in almost everywhere including, home appliances, in constructions, automotives, industrial, aerospace and many other applications. As stated earlier, the conductivity of cis-1,4-polyisoprene (natural rubber) increases by about 100 billion times upon doping with electron acceptors such as iodine. The increase of electrical conductivity, clearly, is relevant to many electrical applications. No reports have so far been made on the mechanical properties of such nonconjugated conductive polymers after doping. Therefore, the possibilities of applications in structural and mechanical areas have not been explored for nonconjugated conductive polymers upon doping. In the present invention, novel results on the mechanical properties of doped nonconjugated conductive polymers are discussed.

The polymers that have been investigated include elastomers such as cis-1,4-polyisoprene, cis-1,4 polybutadiene and styrene-butadiene-copolymers (SBR). The important aspect of all conductive polymers is that the polymer repeat must have at least one double bond. The nonconjugated conductive polymers have at least one isolated double bond in the repeat. Doping of the polymer leads to transfer of an electron from the isolated double bond to the dopant, creating a hole or positive charge at the double-bond site. The hole thus created leads to electrical conduction via intersite hopping as a voltage is applied.

The polymers including natural rubber, polybutadiene and SBR are commercially important for a wide range of applications. In automotive tires alone many billion pounds of these polymers are used per year. Consequently, an improvement of mechanical properties and/or cost reduction can have substantial economic impact in the long term. The results disclosed here show that the mechanical properties of natural rubber, polybutadiene and SBR are substantially enhanced upon doping with chemicals such as iodine prior to curing the polymer. These enhancements include increase of tensile strength, elastic modulus and resilience of the materials. Such characteristics are important for applications in tires and many other products. The details of the measurements have been made on natural rubber and SBR. However, the results should extend to other nonconjugated conductive polymers since all polymers having isolated double bonds are soluble, processable, and having similar properties.

As it is well known, raw natural rubber has little applications since it is tacky, with little resilience. Vulcanization of natural rubber provides the effective elastomeric properties for applications such as in tires. The vulcanization using sulfur leads to cross-linking and enhancement of mechanical properties of rubbers. Besides vulcanization, additives such as carbon black are needed to reduce static electricity and increase strength. The results disclosed here show that iodine doping provides some of the characteristics as imparted by vulcanization and addition of carbon blacks in rubbers.

In addition, vulcanization through iodine doping has other important applications. Waste/scrap tires are known to attract insects such as mosquitoes for breeding. Various types of mosquitoes leading to a number of dangerous diseases are found on scrap tires. The scrap tire piles need to be treated with specific insecticides to reduce these health problems. However, treatment with insecticides often is not hundred percent successful since the insecticides may not reach the depth of the piles where the mosquitoes rest. This problem can be solved by making the tires made in a different way such that the tires repel mosquitoes. Iodine as a dopant or vulcanization agent in tires acts as an insecticide. The tires made by iodine doping or using a mixture of iodine and sulfur overcome the problem of insect-breeding. Iodine doping may lead to other advantages in tire recycling.

DOCTRINE OF EQUIVALENTS

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

EXAMPLE 1

Styrene-butadiene-rubber (SBR) co-polymer samples in the form of latex were obtained from Goodrich Chemical Corp. A thin film of SBR was formed on a tin-oxide coated glass substrate. Then, a thin film of aluminum was deposited on the SBR film such that a "tin-oxide/polymer/Al" junction structure was constructed. This device was enclosed in a glass chamber and a vacuum was applied.

An external voltage was applied on the tin-oxide and aluminum electrodes. Light with a predominantly violet color was observed to emit (electroluminescence) from the polymer as the voltage was increased. The emission intensity was proportional to the voltage applied.

Photoluminescence spectrum of SBR film was recorded using a spectrophotometer. Emission at wavelengths covering 375-475 nm was observed for excitation at 270 nm. The color of the light in electroluminescence is consistent with the photoluminescence spectrum.

SBR film on a glass substrate was doped with iodine leading to a change of color from colorless to black. The electrical conductivity increased by about ten billion times compared to the undoped state to a value of $5 \times 10^{-2}$ S/cm. Thus this is a conductive polymer with isolated double bonds. FTIR spectroscopic studies have shown that doping leads to a reduction of double bonds in SBR due to the formation of radical cations.

EXAMPLE 2

Poly($\beta$-pinene) samples in the form of pellets were obtained from Aldrich Chemical Corp. A thin film of the polymer poly($\beta$-pinene) was formed on a tin-oxide coated glass substrate from a solution in toluene. Then, a thin film of aluminum was deposited on the polymer film such that a "tin-oxide/polymer/Al" junction structure was constructed. This device was enclosed in a glass chamber and a vacuum was applied.

An external voltage was applied on the tin-oxide and aluminum electrodes. Light with a blue-violet color was observed to emit (electroluminescence) from the polymer as the voltage was increased. The emission intensity was proportional to the applied electric field (FIGS. 1 and 2). The maximum of the electroluminescence appeared at 360 nm.

Photoluminescence spectrum of polymer film was recorded using a spectrophotometer. The maximum photoluminescence occurred at 360 nm for excitation at 280 nm. The color of light in electroluminescence is consistent with that of photoluminescence.

Poly($\beta$-pinene) film on a glass substrate was doped with iodine leading to a change of color from colorless to black. The electrical conductivity increased by about ten billion times compared to the undoped state to a value of about $10^{-2}$ S/cm. Thus this is a conductive polymer with isolated double bonds. FTIR spectroscopic studies have shown that doping leads to a reduction of double bonds in the polymer due to the formation of radical cations.

EXAMPLE 3

Cis-1,4 polyisoprene or natural rubber samples were obtained in the form of latex from Firestone Inc. Evaporation of water from a small latex sample led to solid natural rubber. The rubber sample was dissolved in hexane to prepare a solution. Gold electrodes with a gap of approximately 100 microns were deposited on a glass slide. Then a thin film of natural rubber was cast on the electrodes on the glass slide from the hexane solution. The film was about 2 microns in thickness. Upon doping with iodine, the film appeared dark in color.

The doped film was studied for nonlinear optical properties with electric field applied across the gold electrodes. A Helium-Neon laser with wavelength at 633 nm was used for the experiment. The method of measurement included field-induced birefringence in the cross-polarized geometry. This method has been discussed in other reports. In short, the laser beam with polarization at 45° with respect to the applied electric field was passed through the sample. After passing through an analyzer the beam was detected with a photodiode and recorded on an oscilloscope. The modulation signal was recorded on the oscilloscope for various applied ac fields. The signal as obtained for a field of 2 V/$\mu$m is shown in FIG. 3. The lower waveform represents the applied ac field at 4 kHz. The modulation shown in the waveform above (FIG. 3) is due to the quadratic electro-optic effect in the doped polyisoprene film. The modulation signal was also recorded using a lock-in amplifier (with 2 f synchronization). The signal increased quadratically with the applied voltage. A modulation of 0.8% was observed for a field of 2 V/$\mu$m and the film thickness was 2 $\mu$m. The change in refractive index, $\Delta$n, is $4.0 \times 10^{-4}$ at a field of 2.0 V/μm. The magnitude of the quadratic electro-optic effect is exceptionally large. The Kerr constant as determined is about $1.6 \times 10^{-10}$ m/V$^2$. For comparison, the Kerr constant of nitrobenzene at 589 nm is $2.4 \times 10^{-12}$ m/V$^2$. The Kerr constant was determined using the equation: $K=(\Delta n)/(\lambda E^2)$, where $\Delta n$ is the change in refractive index caused by the field, $\lambda$ is the wavelength and E is the electric field. The value is significantly larger than that of the conjugated polymer, polyacetylene, at a wavelength with a similar detuning with respect to the absorption maximum. This is highly unexpected.

Doped polyisoprene absorbs strongly over the wavelength range of 250-625 nm. At an intermediate doping level (iodine molar concentration ~0.3), the lower energy peak appears at 400 nm. At high doping (iodine molar concentration ~0.7), the film becomes dark and absorbs throughout the visible. The experiments performed here involved films with doping levels in the intermediate to high range (molar concentration of 0.3-0.8). The wavelength used (632 nm) was away from the absorption maximum (400-450 nm). The observed Kerr constant is 66 times that of nitrobenzene, one of the best known third order optical material.

The polyisoprene film was also studied using 200 fs laser pulses at 750 nm wavelength. The change in refractive index was measured using Mach-Zhender interferometry as the intensity of the laser beam was increased. A large change in the refractive index was measured consistent with the Kerr coefficient.

The large quadratic electro-optic or third order optical effect has been attributed to the special charge-transfer complex structure and the nano-optical characteristic of the doped polymer.

EXAMPLE 4

Styrene-butadiene-copolymer (SBR) samples were obtained in the form of latex from Goodyear Inc. Evaporation of water from a small latex sample led to solid SBR. The rubber sample was dissolved in hexane to prepare a solution. Gold electrodes with a gap of approximately 100 microns were deposited on a glass slide. Then a thin film of SBR was cast on the electrodes on the glass slide from the hexane solution. The film was about 3 microns in thickness. Upon doping with iodine, the film appeared dark in color.

The doped film was studied for nonlinear optical properties with electric field applied across the gold electrodes. A Helium-Neon laser with wavelength at 633 nm was used for the experiment. The method of measurement included field-induced birefringence in the cross-polarized geometry. This method has been discussed in other reports. In short, the laser beam with polarization at 45° with respect to the applied electric field was passed through the sample. After passing through an analyzer the beam was detected with a photodiode and recorded on an oscilloscope. The modulation signal was recorded on the oscilloscope for various applied ac fields. A modulation depth of about 1% was observed for a field of 2 V/μm.

Doped SBR absorbs strongly over the wavelength range of 250-610 nm. At an intermediate doping level, the lower energy peak appears at 395 nm. At high doping, the film becomes dark and absorbs throughout the visible. The experiments performed here involved films with doping levels in the intermediate to high range. The wavelength used (632 nm) was away from the absorption maximum (395-410 nm). The observed Kerr constant is about 58 times that of nitrobenzene, one of the best known third order optical material.

The SBR film was also studied using 200 fs laser pulses at 750 nm wavelength. The change in refractive index was measured using Mach-Zhender interferometry as the intensity of the laser beam was increased. A large change in the refractive index was measured consistent with the Kerr coefficient.

The large quadratic electro-optic or third order optical effect has been attributed to the special charge-transfer complex structure and the nano-optical characteristic of the doped polymer.

EXAMPLE 5

Poly(β-pinene) samples were obtained in the form of pellets from Aldrich Chemicals Inc. Gold electrodes with a gap of approximately 100 microns were deposited on a glass slide. A thin film of the polymer poly(β-pinene) was formed on the glass substrate from a solution in toluene. The film was about 1 micron in thickness. Upon doping with iodine, the film appeared dark in color.

The doped film was studied for nonlinear optical properties with electric field applied across the gold electrodes. A Helium-Neon laser with wavelength at 633 nm was used for the experiment. The method of measurement included field-induced birefringence in the cross-polarized geometry. This method has been discussed in other reports. In short, the laser beam with polarization at 45° with respect to the applied electric field was passed through the sample. After passing through an analyzer the beam was detected with a photodiode and recorded on an oscilloscope. The modulation signal was recorded on the oscilloscope for various applied ac fields. A modulation depth of about 0.12% was observed for a field of 1.25 V/μm.

Doped SBR absorbs strongly over the wavelength range of 250-610 nm. At an intermediate doping level, the lower energy peak appears at 400 nm. At high doping, the film becomes dark and absorbs throughout the visible. The experiments performed here involved films with doping levels in the intermediate to high range. The wavelength used (633 nm) was away from the absorption maximum (395-410 nm). The observed Kerr constant is about 50 times that of nitrobenzene, a standard third order optical material.

The SBR film was also studied using 200 fs laser pulses at 750 nm wavelength. The change in refractive index was measured using Mach-Zhender interferometry as the intensity of the laser beam was increased. A large change in the refractive index was measured consistent with the Kerr coefficient.

The large quadratic electro-optic or third order optical effect has been attributed to the special charge-transfer complex structure and the nano-optical characteristic of the doped polymer.

EXAMPLE 6

Poly(β-pinene) samples were obtained in the form of pellets from Aldrich Chemicals Inc. Gold electrodes with a gap of approximately 100 microns were deposited on a glass slide. A thin film of the polymer (poly(β-pinene) was formed on the glass substrate from a solution in toluene. The film was about 1 micron in thickness. The film was doped with antimony pentachloride. Upon doping the film became dark in color.

The doped film was studied for nonlinear optical properties with electric field applied across the gold electrodes. A Helium-Neon laser with wavelength at 633 nm was used for the experiment. The method of measurement included field-induced birefringence in the cross-polarized geometry. This method has been discussed in other reports. In short, the laser beam with polarization at 450° with respect to the applied electric field was passed through the sample. After passing through an analyzer the beam was detected with a photodiode and recorded on an oscilloscope. The modulation signal was recorded on the oscilloscope for various applied ac fields. A modulation depth of about 0.14% was observed for a field of 1.25 V/μm.

Doped SBR absorbs strongly over the wavelength range of 250-610 nm. At an intermediate doping level, the lower energy peak appears at 400 nm. At high doping, the film becomes dark and absorbs throughout the visible. The experiments performed here involved films with doping levels in the intermediate to high range. The wavelength used (632 nm) was away from the absorption maximum (395-410 nm). The observed Kerr constant is about 58 times that of nitrobenzene, a standard third order optical material.

The SBR film was also studied using 200 fs laser pulses at 750 nm wavelength. The change in refractive index was measured using Mach-Zhender interferometry as the intensity of the laser beam was increased. A large change in the refractive index was measured consistent with the Kerr coefficient.

The large quadratic electro-optic or third order optical effect has been attributed to the special charge-transfer complex structure and the nano-optical characteristic of the doped polymer.

EXAMPLE 7

Natural rubber (cis-1,4 polyisoprene) sample in the form of latex was obtained from Firestone Inc. Solid specimens of specific sizes and shapes were prepared by casting of the latex on a Teflon-coated aluminum substrate and by evaporation of the water. The samples were doped with iodine at different molar concentrations. The mechanical testing of the sample before and after iodine doping was performed using a Instron equipment. In the undoped state, polyisoprene is a tacky and ductile solid with a relatively low modulus (~13 MPa). After doping, the samples become mechanically much stronger (modulus—53 MPa). The doped sample was treated with a solvent such as hexane to extract the residual unreacted iodine. Then the film was observed to have the characteristic of a rubber band with excellent elastomeric property. Similar elastomeric property is also produced by doping with a controlled amount of iodine such that no residual unreacted iodine exists in the polymer. The doping has a similar effect as vulcanization along with strengthening using fillers.

EXAMPLE 8

Styrene-butadiene-copolymer (SBR) sample in the form of latex was obtained from Goodyear Inc. Solid specimens of specific sizes and shapes were prepared by casting of the latex on a Teflon-coated aluminum substrate and by evaporation of the water. The samples were doped with iodine at different molar concentrations. The mechanical testing of the sample before and after iodine doping was performed using a Instron equipment. In the undoped state, SBR is a ductile solid with a relatively low modulus (~30 MPa). After doping, the samples become mechanically much stronger (modulus~153 MPa). Removing the residual unreacted iodine with solvents such as hexane significantly enhanced the elastomeric property of the sample.

EXAMPLE 9

Natural rubber (cis-1,4 polyisoprene) sample in the form of latex was obtained from Firestone Inc. Solid specimens of specific sizes and shapes were prepared by casting of the latex on a Teflon-coated aluminum substrate and by evaporation of the water. A mixture of sulfur and iodine with a higher content of sulfur was heated to form a dark material. This material was applied all around a rubber specimen. Then the sample was heated for vulcanization. The time required for completion of vulcanization was found to be significantly shorter than using sulfur alone. The mechanical properties of this vulcanized sample were similar to that of rubber vulcanized with sulfur and carbon black. The presence of iodine in the vulcanized rubber acts as an insecticide.

The characteristics of the nonconjugated polymers and their advantages in the above applications are as follows:
1. Electric field-induced emission of light has been observed in nonconjugated conductive polymers.
2. The basic light-emitting device is constructed by forming a junction consisting of "high work-function metal/polymer/low work-function metal."
3. Electric field is applied on the metal electrodes leading to light emission.
4. The intensity of the emitted light is proportional to the applied electric field.
5. The copolymer (styrene-butadiene-rubber), SBR, gives light emission in the violet-blue region.
6. The polymer poly(β-pinene) gives light emission in the blue-violet region.
7. Large third order optical effects including quadratic electro-optic coefficients have been observed in nonconjugated conductive polymers after doping.
8. The magnitude of the Kerr coefficient in doped cis-1,4 polyisoprene (natural rubber) is 66 times larger than that of nitrobenzene.
9. The magnitude of the Kerr constant in doped SBR is 58 times that of nitrobenzene.
10. The magnitude of the Kerr coefficient of poly(β-pinene) is 50 times that of nitrobenzene.
11. Enhanced mechanical/elastomeric properties are obtained upon doping of nonconjugated conductive polymers.
12. The elastic modulus in SBR increased about five times upon doping with iodine.
13. The elastic modulus of cis-1,4 polyisoprene (natural rubber) increased about four times upon doping with iodine.
14. The doping of natural rubber has a similar effect as vulcanization using sulfur along with strengthening with fillers.
15. The doping of SBR has a similar effect as vulcanization and strengthening with fillers.
16. The vulcanization of natural rubber with a heated mixture of sulfur and iodine leads to a faster rate of vulcanization.
17. Use of iodine along with sulfur in vulcanization overcomes the problem of insect-breeding (mosquitoes) on used tires.

The invention claimed is:

1. A light emitting structure comprising a substrate selected from the group consisting of quartz and glass, said substrate coated with a high work function metal coating or metal oxide coating which has a conductive polymer film formed on the metal coating or metal oxide coating, said conductive polymer film consisting of a styrene-butadiene-rubber copolymer, and a low work function metal deposited on the conductive polymer film.

2. The light emitting structure of claim 1 in which the substrate is quartz.

3. The light emitting structure of claim 2, in which the high work function metal oxide coating is indium tin oxide.

4. The light emitting structure of claim 2, in which the low function metal is selected from the group consisting of aluminum, calcium and magnesium.

5. The light emitting structure of claim 1, in which the substrate is glass.

6. The light emitting structure of claim 5, in which the high work function metal oxide coating is indium tin oxide.

7. The light emitting structure of claim 5, in which the low function metal is selected from the group consisting of aluminum, calcium and magnesium.

8. A light emitting structure comprising a substrate selected from the group consisting of quartz and glass, said substrate coated with a high work function metal coating or metal oxide coating which has a conductive polymer film formed on the metal coating or metal oxide coating, said conductive polymer film consisting of poly($\beta$-pinene), and a low work function metal deposited on the conductive polymer film.

9. A light emitting structure comprising a quartz substrate, said substrate coated with a high work function metal coating or metal oxide coating which has a conductive polymer film formed on the metal coating or metal oxide coating, said conductive polymer film consisting of a poly($\beta$-pinene) polymer, and a low work function deposited on the conductive polymer film.

10. A light emitting structure comprising a guartz substrate, said substrate coated with indium tin oxide which has a conductive polymer film selected from the group consisting of styrene-butadiene-rubber copolymer and poly($\beta$-pinene), and a low work function metal selected from the group consisting of aluminum, calcium and magnesium deposited on the conductive polymer film.

11. A light emitting structure comprising a glass substrate, said substrate coated with a high work function metal coating or metal oxide coating which has a conductive polymer formed on the metal coating or metal oxide coating, said conductive polymer film consisting of a poly($\beta$-pinene) copolymer, and a low work function metal deposited on the conductive polymer film.

12. A light emitting structure comprising a glass substrate, said substrate coated with indium tin oxide which has a conductive polymer film formed on the indium tin oxide coating, said conductive polymer film is selected from the group consisting of styrene-butadiene-rubber copolymer and poly($\beta$-pinene), and a low work function metal selected from the group consisting of aluminum, calcium and magnesium which is deposited on the conductive polymer film.

* * * * *